United States Patent [19]

Uhing et al.

[11] E Re. 31,300

[45] Reissued * Jul. 5, 1983

[54] PROCESS FOR PREPARING ALKYL- OR ARYLPHOSPHONOTHIOIC DIHALIDES

[75] Inventors: Eugene H. Uhing, Pleasantville, N.Y.; Arthur D. F. Toy, Stamford, Conn.

[73] Assignee: Stauffer Chemical Company, Westport, Conn.

[ * ] Notice: The portion of the term of this patent subsequent to Jul. 29, 1992, has been disclaimed.

[21] Appl. No.: 1,633

[22] Filed: Jan. 5, 1979

Related U.S. Patent Documents

Reissue of:

[64] Patent No.: 3,968,156
Issued: Jul. 6, 1976
Appl. No.: 534,942
Filed: Dec. 20, 1974

[51] Int. Cl.[3] ..... C07F 9/42
[52] U.S. Cl. ..... 260/543 P
[58] Field of Search ..... 260/543 P

[56] References Cited

U.S. PATENT DOCUMENTS 3,294,745 12/1966 Wismer ..... 260/543 P X
3,803,226 4/1974 Uhing et al. ..... 260/543 P
3,897,491 7/1975 Toy et al. ..... 260/543 P
4,076,746 2/1978 Toy et al. ..... 260/543 P

FOREIGN PATENT DOCUMENTS 1238024 12/1974 Fed. Rep. of Germany ... 260/543 P
332095 4/1972 U.S.S.R. ..... 260/543 P

OTHER PUBLICATIONS

Topics in Phosphorus Chemistry, vol. 8, p. 235 to p. 243, p. 242 pertinent.

*Primary Examiner*—Ethel G. Love
*Attorney, Agent, or Firm*—Paul J. Juettner

[57] ABSTRACT

Alkyl- or arylphosphonothioic dihalides are prepared by contacting an alkyl or aryl halide with a trivalent phosphorus compound having three halogens attached thereto or a pentavalent thiophosphorus halide having three halogens attached thereto or mixtures of the trivalent and pentavalent phosphorus halides, in the presence of phosphorus sulfides, for example, $P_4S_3$, $P_4S_7$ or $P_4S_{10}$ under at least autogenous pressure at a temperature of from about 175° C. to about 400° C. The compounds obtained are useful as constituents in insecticides, fungicides, pharmaceuticals, and as intermediates in preparation of other organophosphorus compounds.

6 Claims, No Drawings

PROCESS FOR PREPARING ALKYL- OR ARYLPHOSPHONOTHIOIC DIHALIDES

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a new and improved process for the preparation of alkyl- or arylphosphonothioic dihalides.

2. The Prior Art

Alkylphosphonothioic dihalides have been prepared in the prior art by reacting alkyl halides with phosphorus trihalides in the presence of aluminum chloride. The reaction proceeds at room temperature according to the formula set forth in Heuben-Weyl, Methoden der Organis Chenchemie, Volume 12, part 1 (1965) at page 396.

$$xRCl + PCl_3 + AlCl_3 \longrightarrow xRPCl_4, AlCl_3 \xrightarrow{(x+1)H_2O} \underset{\substack{\uparrow \\ O}}{xRPCl_3} + AlCl_3, xH_2O + 2xHCl \quad (1)$$

The Heuben-Weyl reference also notes that the reaction has been attempted in the absence of the aluminum chloride catalyst with little success. The alkylphosphonothioic dihalides are prepared by replacing the oxygen of the alkylphosphonic dihalide with sulfur as shown on page 553 of the Heuben-Weyl reference. The yields of the replacement reaction are limited to the yields obtained in the initial reaction forming the alkylphosphonic dihalide.

Phosphorus sulfides are known in the form of four well-characterized crystalline compounds, namely, $P_4S_{10}$, $P_4S_7$, $P_4S_5$ and $P_4S_3$. Of these, $P_4S_{10}$ and $P_4S_3$ are produced commercially.

It is known that alkyl- or arylphosphonous dichlorides can be prepared from an alkyl or aryl halide, phosphorus trichloride and phosphorus at elevated temperatures in an autoclave and under autogenous pressure ("Synthesis of Alkyl- and Arylphosphorus Dichlorides and Dibromides"—Zhurnol Obshchei Khimii, Vol. 37 No. 4, pp. 890–892, Apr. 1967).

A method of preparing alkyl- or arylphosphonothioic dihalides according to the following reaction scheme:

$$3RX + aPX_3 + bP(S)X_3 + (0.3a + 0.2b)P_4S_{10} + (0.8a + 1.2b)P \rightarrow 3RP(S)X_2 \quad (2)$$

where $a+b=1$, is described in U.S. Pat. No. 3,803,226. That method, however, has the disadvantage that yellow phosphorus must be handled to effect the reaction.

SUMMARY OF THE INVENTION

In accordance with the present invention, there is provided a new method for preparing compounds of the formula:

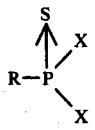

(1)

wherein R is a hydrocarbyl group consisting of hydrogen and carbon including $C_1$ to $C_{20}$ alkyl and the aryl (1 and 2 fused rings) substituted derivatives thereof, cycloalkyl of 5–6 carbons in the ring, aryl of up to 3 fused rings or biphenyl and the $C_1$–$C_4$ alkyl substituted derivatives of said cycloalkyl, aryl, or biphenyl and X is chlorine or bromine.

Typical alkyl groups include methyl, ethyl, n-propyl and isopropyl, n-butyl, isobutyl, tert-butyl, pentyl, hexyl, heptyl, octyl, nonyl, decyl, dodecyl, tetradecyl, hexadecyl, octadecyl and eicosyl. Some suitable aralkyl groups are phenylmethyl, phenylethyl, phenylbutyl, phenyloctyl, phenylhexadecyl, and the corresponding naphthyl derivatives. Ring systems wherein R is cycloalkyl having 5–6 carbons in the ring are illustrated by cyclopentyl and cyclohexyl and its derivatives.

Examples of aryl and substituted aryl groups include phenyl, methylphenyl, ethylphenyl, propylphenyl, butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl, and the like. Any of said groups can contain one or more alkyl radicals and any isomeric form of said groups can be used.

Biphenyl R groups include the $C_1$ to $C_4$ alkyl substituted derivatives such as methylbiphenyl and ditolyl. There can be one or more substituents as desired and said substituents can be in any isomeric position desired. The R groups also can be connected to the phosphorus at any isomeric position.

With respect to X, chlorine is preferred over bromine as it is inexpensive and reacts readily. Bromine, however, can be used if it is desired to have bromine in the final compound. Also, bromine is useful in the preparation of bromine containing intermediates for flame retardant compounds.

The method of the present invention comprises contacting an alkyl or aryl halide reactant of the formula:

$$RX \quad (II)$$

with a trivalent phosphorus reactant of the formula:

$$PX_3 \quad (III)$$

or a pentavalent thiophosphoryl halide reactant of the formula:

$$P(S)X_3 \quad (IV)$$

or mixtures of the trivalent and pentavalent phosphorus halides in the presence of the phosphorus sulfides $P_4S_3$, $P_4S_5$, $P_4S_7$ or $P_4S_{10}$ wherein R and X are as defined above. Any combination of phosphorus sulfides can be used in appropriate quantities to give the P:S ratio desired for a reaction.

Representative compounds within the formula (II) include methyl chloride, propyl chloride, butyl chloride, octyl chloride, decyl chloride, dodecyl chloride, hexadecyl chloride, octadecyl chloride, eicosyl chloride, and the corresponding bromo substituted derivatives; chlorocyclopentane, chlorocyclohexane and the corresponding bromo substituted derivatives; chlorobenzene, bromobenzene, chlorotoluene, (chloro) ethylbenzene, (bromo) ethylbenzene, (chloro) propylbenzene, (bromo) propylbenzene, (chloro) butylbenzene, (bromo) butylbenzene, chloronaphthalene, bromonaphthalene, (chloro) methylnaphthalene, (bromo) methylnaphthalene, (chloro) naphthylene, (bromo) ethylnaphthalene, (chloro) propylnaphthalene, (bromo) butylnaphthalene, chloroanthracene, (chloro) methylanthracene, bromoanthracene, (chloro) butylanthracene, chlorodimethylbenzene, bromodimethylnaphthalene, chlorodiethylanthracene, and the like. In the aliphatic series above the $C_2$ alkyl and in the aromatic series, isomeric forms of the same halide compound are formed. These are intended to be included in the definition of said halide compound. The foregoing compounds are given as illustrative and are in no way considered to be totally inclusive of all of the alkyl and aryl halides which can be used in the method of the present invention.

In the trivalent phosphorus halide depicted by the Formula (III), the three halogens preferably are the same halogen although mixed halogens can be used. The chlorine derivative is preferred for the reasons previously set forth in this specification. The bromine species, however, can be prepared if desired.

In the pentavalent thiophosphoryl halide depicted by the Formula (IV), the three halogens preferably are the same halogen although mixed halogen compounds can be used. Again, the chlorine derivative is preferred, but the bromine species can be used if desired. Representative pentavalent thiophosphoryl halides are thiophosphoryl chlorodibromide, and thiophosphoryl bromodichloride. For economic reasons, thiophosphoryl chloride or thiophosphoryl bromide is preferred. Mixtures of the pentavalent thiophosphoryl halide can be used without departing from the scope of the invention.

The phosphorus sulfides, $P_4S_3$, $P_4S_5$, $P_4S_7$ and $P_4S_{10}$ are known. Of these, $P_4S_3$ and $P_4S_{10}$ can be readily obtained commercially and therefore are preferred for economic reasons. However, phosphorus sulfides having a specific phosphorus to sulfur ratio can be prepared by reacting the appropriate quantity of phosphorus and sulfur.

Stoichiometrically, the process of the present invention appears to require a ratio of three moles of alkyl or aryl halide per mole of the trivalent phosphorus halide or pentavalent thiophosphoryl halide or per mole of a mixture of said phosphorus halide and said pentavalent thiophosphoryl halide, in addition to the phosphorus sulfides. For example, as the amount of pentavalent thiophosphoryl halide increases, the amount of trivalent phosphorus halide decreases, the amount of $P_4S_7$ decreases and the amount of $P_4S_3$ increases. Some theoretical reaction schemes can be postulated as follows:

$$3RX + aPX_3 + bP(S)X_3 + \frac{(3-2b)}{14} P_4S_{10} + \frac{2+b}{7} P_4S_3 \longrightarrow 3RP(S)X_2 \quad (3)$$

or $$3RX + aPX_3 + bP(S)X_3 + \frac{(3-2b)}{8} P_4S_3 + \frac{(2b+1)}{8} P_4S_3 \longrightarrow 3RP(S)X_2 \quad (4)$$

wherein R and X are as defined above and a+b=1. Other reaction schemes can be postulated for various combinations of phosphorus sulfides in accordance with the following general scheme:

$$3RX + aPX_3 + bP(S)X_3 + \frac{[P_4S_{(6-2b)}]}{2} \longrightarrow [3RP(S)Cl_2]\,3RP(S)X_2 \quad (5)$$

where a+b=1.

The mechanism of the reaction is not completely understood. As this reaction scheme is postulated only, applicants do not intend to limit their process thereto. The amounts given in the theoretical scheme, however, or those approximately approaching said amounts should be used for efficiency and to avoid by-product formation and the need for extensive product purification and excess reactant recovery.

It is also to be understood that the process of the present invention can proceed either with the trivalent phosphorus halide or the thiophosphoryl halide alone or mixtures thereof. Any stoichiometric amounts of these reactants can be used though it is preferred that the additive molar total of these reactants equals about one, as set-forth hereinbefore, so as to avoid the necessity of separating unreacted starting material.

The process of the present invention is carried out at elevated temperature and at least at autogenous pressure. Temperatures of from about 175° C. to about 400° C. and preferably from about 220° C. to about 350° C. are generally employed. The pressures can be from about 1 to about 300 atmospheres although pressures from about 10 to about 100 atmospheres are generally utilized.

Reaction times can vary over relatively wide ranges and can easily be determined by one skilled in the art. Factors affecting reaction time include reactivity of the reactants and temperature. For example, reactivity of alkyl halides increases with chain length and reaction time therefore decreases accordingly. Reaction time generally decreases with increases in reaction temperature. Typical reaction times are from about 1 to about 24 hours.

The process of the present invention can conveniently be effected by introducing the individual reactants into a reaction zone capable of withstanding elevated pressure, such as a metal bomb, autoclave, or other pressure vessel, and carrying out the reaction under at least the autogenous pressure developed by the reactants at the reaction temperature. An agitation means should be provided for said reaction zone.

The products of the reaction are purified by conventional methods such as by fractional distillation of liquids and sublimation, crystallization or extraction of solid products.

The identification of products is achieved by conventional methods, such as elemental analysis, and gas chromatography for purity and mass spectrometer and nuclear magnetic resonance and infrared analysis to establish structure.

Illustrative of the compounds which can be prepared by the method of the present invention are:

Alkyl $CH_3P(S)Cl_2$
$CH_3P(S)Br_2$
$C_2H_5P(S)Cl_2$
$C_2H_5P(S)Br_2$
$C_3H_7P(S)Cl_2$
$C_2H_9P(S)Cl_2$
$C_4H_9P(S)Br_2$
$C_5H_{11}P(S)Cl_2$
$C_8H_{17}P(S)Cl_2$
$C_8H_{17}P(S)Br_2$
$C_{18}H_{37}P(S)Cl_2$
$(CH)_3CCH_2P(S)Cl_2$ CYCLIC COMPOUNDS
Aromatic Series Benzene Series:

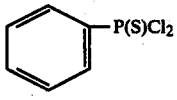

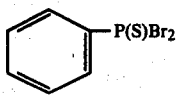

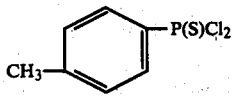

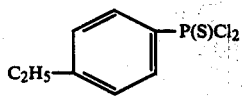

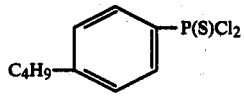

Naphthalene series:

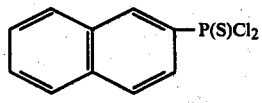

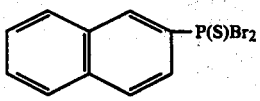

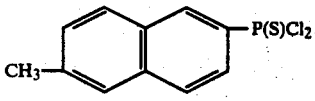

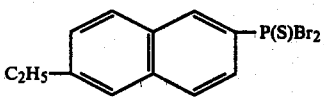

Anthracene series:

-continued
CYCLIC COMPOUNDS
Aromatic Series

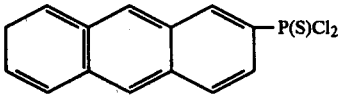

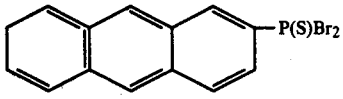

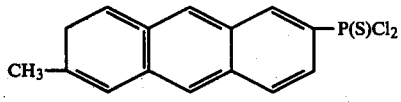

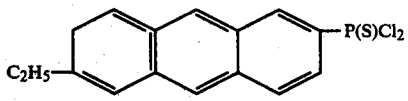

Biphenyl series:

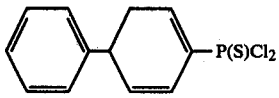

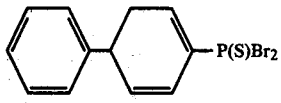

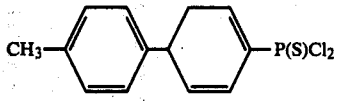

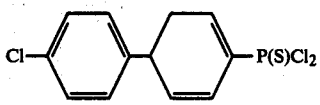

Aliphatic series:
5 membered carbon ring:

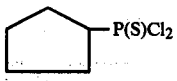

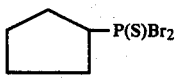

6 membered carbon ring:

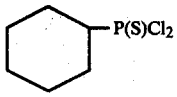

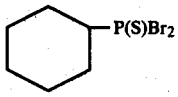

The products of the present invention are dihalides of pentavalent phosphorus and, therefore, can be subject to all the known reactions which such compounds undergo. Said products can be used to make insecticides as illustrated by the process for making O-ethyl O-paranitrophenyl phenyl-phosphonothioate as per the following illustrative reaction scheme:

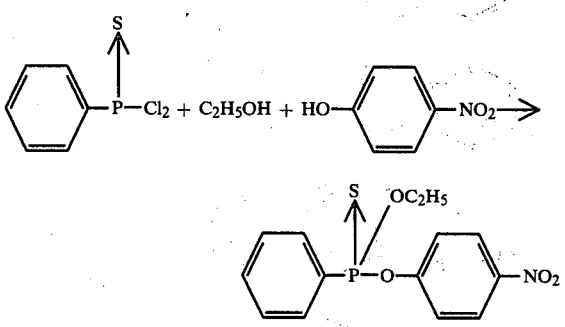

and for making O-ethyl S-phenyl ethylphosphonothioate as per the following illustrative reaction scheme:

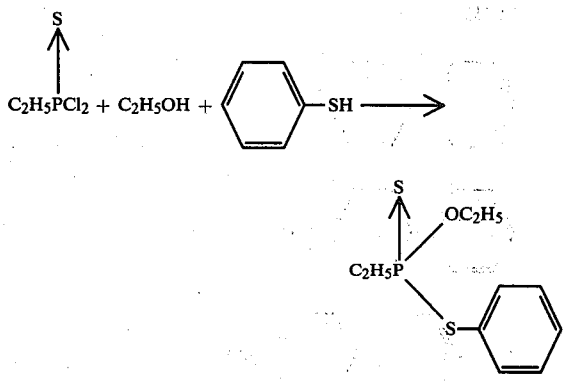

The present invention will be more fully illustrated in the examples which follow.

EXAMPLE I

In a 300-ml. 316 stainless steel autoclave is placed 65.7 g $CH_3Cl$ (1.3 mole); 59.6 g $PCl_3$ (0.435 mole); 56.7 g $P_4S_7$ (0.163 mole); and 12 g $P_4S_3$ (0.0545 mole). Heat of reaction is maintained at 340° C. for 3.25 hours. The crude yield is 182 grams.

The crude product has the following analysis by glc with internal standard.

| Component | Weight % |
|---|---|
| $PCl_3$ | 4.9 |
| $P(S)Cl_3$ | 4.4 |
| $CH_3P(S)Cl_2$ | 69.3 |
| $(CH_3)_2P(S)Cl$ | 9.8 |

The crude product is then distilled to yield 120 g methylphosphonothioic dichloride (62% yield) (b.p. 10 mm Hg pressure=36° C. $n_D^{25}=1.5470$). The structure of the product is confirmed by H-nmr.

EXAMPLE II

In a 300-ml. 316 stainless steel autoclave is placed 69 g $C_2H_5Cl$ (1.07 mole); 45.9 g $PCl_3$ (0.335 mole); 43.5 g $P_4S_7$ (0.125 mole); and 9.2 g $P_4S_3$ (0.0419 mole).

The autoclave is heated to 330° C. for 12 hours. The weight of liquid poured from the autoclave is 140.5 g. Analysis by glc with internal standard gives the following results.

| Component | Weight % |
|---|---|
| $PCl_3$ | 3.9 |
| $P(S)Cl_3$ | 1.5 |
| $C_2H_3P(S)Cl_2$ | 63.1 |
| $(C_2H_3)_2P(S)Cl$ | 5.0 |

The product is distilled to give 79 g ethylphosphonothioic dichloride (47.5% yield) (b.p. at 10 mm Hg pressure=55° C.; $n_D^{20}=1.5430$).

EXAMPLE III

A mixture of n-propyl chloride (78.5 g, 1 mole), $PCl_3$ (45.9 g, 0.333 mole), $P_4S_7$ (43.5 g, 0.125 mole), and $P_4S_3$ (9.2 g, 0.418 mole) is heated at 305° C. for 12 hours. Upon cooling and venting, 0.17 mole (6.2 g) of HCl is collected in an aqueous NaOH trap. The liquid poured out from the autoclave weighs 163.9 g, which with the 6.2 g of HCl collected accounts for 170.1 g of the original input of 177.1 g of reactants.

The liquid is fractionated, collecting a fraction with a boiling range of 75°–85° C. at 12 mm (86.5 g). The second fraction is collected at a vapor temperature range of 64°–165° C. at 0.05 mm with the pot temperature up to 190° C. It weighs 52.2 g. The residue left weighs 13.7 g and a volatile fraction collected in the liquid nitrogen-cooled trap weighs 11.5 g. This volatile fraction is shown by glc to contain 10.4 g (0.076 mole) of unreacted $PCl_3$, or 22.9% of the original input. There is also 1.1 g (0.0065 mole) of $P(S)Cl_3$.

The first fraction is redistilled using a 3-ft. column and collecting the main fraction; b.p. 26° C. at 0.01 mm, $n_D^{25}$ 1.5315. It weighs 83 g (0.47 mole), or a yield of 47% based on the phosphorus content of the reactants.

| Analysis |
|---|
| Calc'd. for $C_3H_7P(S)Cl_2$; P, 17.5; S, 18.05; Cl, 40.1 |
| Found: P, 16.8; S, 17.7; Cl, 39.5 |

Analysis of the product by $^1H$ nmr shows that the major component is i-propylphosphonothionic dichloride and that the n-propylphosphonothionic dichloride is present only as a minor component. These results show that the n-propyl group in the starting material, n-propyl chloride, is greatly isomerized during some stages of the reaction.

EXAMPLE IV

This reaction is carried out under the same conditions as that for n-propyl chloride, using the identical quantity of reactants except that isopropyl chloride is used in place of the n-propyl chloride. Upon venting of the autoclave, 0.19 mole (6.9 g) of HCl is collected in the aqueous trap. The liquid poured from the autoclave weighs 162 g. This along with the collected HCl accounts for 168.9 g of the 177.1 g of reactants used. The liquid is distilled, collecting a first fraction with a boiling range of 75°–110° C. at 12 mm (84 g) and a second fraction with a boiling range of 80°–175° C. at 0.05 mm (45.5 g). The residue left weighs 17 g. There is also collected 11.5 g of liquid in the liquid nitrogen-cooled trap. This liquid, based on glc analysis, contains 9.9 g (0.072 mole) of unreacted $PCl_3$, or 21.5% of the original input. The other components are small quantities of $P(S)Cl_3$ and $i\text{-}C_3H_7P(S)Cl_2$.

The first fraction is redistilled using a 3-ft. column and the main fraction collected (b.p. 26° C. at 0.1 mm, $n_D^{25}=1.5315$) weighs 77 g, or a yield of 43.5% based on the phosphorus content of the reactants.

| Analysis |
|---|
| Cal'c. for $(CH_3)_2CHP(S)Cl_2$; P, 17.5; S, 18.05; Cl, 40.1 |
| Found: P, 17.5; S, 18.2; Cl, 40.6. |

$^1H$ nmr analysis shows the compound to be mainly the excepted $i\text{-}C_3H_7PSCl_2$. However, it also shows a minor quantity of $n\text{-}C_3H_7PSCl_2$, thus indicating some minor isomerization of the isopropyl group.

EXAMPLE V

A mixture of t-butyl chloride (92.6 g, 1 mole), $PCl_3$ (45.9 g, 0.333 mole), $P_4S_7$ (43.5 g, 0.125 mole) and $P_4S_3$ (9.3 g, 0.0418 mole) is heated at 270°-280° C. for 12 hours. Upon cooling and venting, 0.21 mole (7.7 g) of HCl is collected. The 173 g of reaction product is poured out from the autoclave and is first analyzed by glc and then distilled. Glc analysis indicates the presence of unreacted t-butyl chloride, but the absence of any rearranged t-butyl chlorides. Upon distillation, the first fraction, with a boiling range of 84°-100° C. at 12 mm, weighs 94 g. The second fraction, boiling at 82°-180° C. at 0.5 mm, weighs 32 g. The residue weighs 22 g. There is also collected in the dry-ice acetone-cooled trap 15.5 g of liquid. Lost on distillation is 9.5 g of volatiles. The liquid collected in the cold trap is analyzed by glc and shown to contain 12.4 g (0.13 mole) of unreacted t-butyl chloride (by $^1H$ nmr), 1.8 g $PSCl_3$, and small quantities of $PCl_3$ and $C_4H_9P(S)Cl_2$.

The first fraction is a colorless liquid containing some colorless crystals. Analysis by $^{31}P$ nmr shows it to contain $(CH_3)_3C\text{-}P(S)Cl_2$ and $$(CH_3)_2\overset{\overset{\displaystyle H}{|}}{C}CH_2-P(S)Cl_2$$

in an approximate ratio of 1:1.8. The crystals are filtered, dried and sublimed at 40° C. and 0.05 min; m.p. 176° C. The m.p. reported in the literature for $t\text{-}C_4H_9P(S)Cl_2$ is 172.5°-175° C. Analysis by $^{13}C$ nmr shows the following coupling constants in Hz: $J^1_{CP}$, 59; $J^2_{CP}$, <6; $J_{CH3}$, ~125; $J^1_{CC}$, 5. For $^{31}P$, chemical shifts from $H_3PO_4$ is −116. The value reported in the literature for $t\text{-}C_4H_9\text{-}P(S)Cl_2$ is −114.5.

| Analysis |
|---|
| Calc'd. for $(CH_2)_3CP(S)Cl_2$; P, 16.2; s, 16.7; Cl, 37. |
| Found: P, 16.1; S, 16.4; Cl, 36.2. |

The first fraction is further fractionated, and a liquid fraction isolated (b.p. 35° C. at 0.1 mm), freed of solid, is obtained.

| Analysis |
|---|
| Calc'd. for $C_4H_9P(S)Cl_2$; P, 16.2; Cl, 37.2; S, 16.75. |
| Found: P, 16.1; Cl, 36.9; S, 16.9. |

Analysis by $^{13}C$ nmr indicates that the liquid product is a mixture of $(CH_3)_3C\text{-}P(S)Cl_2$ and $(CH_3)_2CHCH_2P(S)Cl_2$ at a ratio of approximately 1:3.

The $^{13}C$ nmr shows that the $(CH_3)_2CHCH_2P(S)Cl_2$ has the following coupling constants in Hz: $J^1_{CP}$, 68; $J^2_{CP}$, <6; $J_{pCH}$, 137.5; $J_{CH3}$, ~125; $J^1_{CC}$, 6; $J^2_{CC}$, 12. For $^{31}P$, chemical shifts from $H_3PO_4$, −90.8.

The second fraction obtained in the original distillation which weighs 32 g is furthr fractionated at 0.1 mm collecting 5 fractions: (a) b.p. to 92° C., 6.5 g; (b) b.p. 96°-100° C. 7 g; (c) 101°-125° C., 4 g; (d) b.p. 125°-130° C., 3.5 g and (e) 130°-170° C., 3.5 g.

The preceding reaction is repeated at a lower temperature (240° C. for 12 hours) to check the effect of temperature on the relative proportion of $t\text{-}C_4H_9P(S)Cl_2$ and $(CH_3)_2CHCH_2P(S)Cl_2$ in the product. When the reaction is completed, venting of the autoclave results in the trapping of 4.2 g of HCl and 7 g of other volatile material. The dark reaction product is a liquid-solid mixture weighing 163 g (total original reactants weighed 191 g). The solid is removed by filtration. It weighs 70 g, which upon sublimination under reduced pressure yields 67 g of white crystalline $t\text{-}C_4H_9P(S)Cl_2$. The filtrate is distilled. The first fraction collected, b.p. 90°-105° C. at 12 mm, consists of a solid-liquid mixture weighing 32 g, which upon filtration yields 6 g more of solid $t\text{-}C_4H_9P(S)Cl_2$ and 26 g of filtrate which, based on the data from the preceding experiment, is assumed to be $(CH_3)_2CHCH_2\text{-}P(S)Cl_2$ with some dissolved $t\text{-}C_4H_9P(S)Cl_2$. A second fraction collected, b.p. 90°-150° C. at 0.1 mm, weighing 20 g probably consists primarily of $(C_4H_9)_2P(S)Cl$ and $Cl_2P(S)C_4H_8P(S)Cl_2$. The residue left weighs 8 g.

The total isolated solid $t\text{-}C_4H_9P(S)Cl_2$ of 73 g from this experiment represents a yield 38% of theory, while the yield of impure $(CH_3)_2CHCH_2P(S)Cl$ weighs only 26 g or 13.5% of theory. The yield of solid $t\text{-}C_4H_9P(S)Cl_2$ from this reaction is therefore considerably higher than that of the liquid $(CH_3)_2CHCH_2P(S)Cl_2$. In other words, when the original reaction is carried out at a lower temperature, less isomerization to $(CH_3)_2CHCH_2P(S)Cl_2$ occurs.

To further check the effect of lower reaction temperature on the relative ratio of $T\text{-}C_4H_9P(S)Cl_2$ to $(CH_3)_2CHCH_2P(S)Cl_2$ in the product, the reaction is carried out at a lower temperature, 220° C. for 12 hours (using one-half the amount of reactants as in the preceding two experiments). Upon venting, 0.057 mole or 2.08 g of HCl is collected. The reaction product is a solid which upon sumlimation yields 55 g of solid $T\text{-}C_4H_9P(S)Cl_2$. This yield is 58% of theory. No liquid $(CH_3)_2CHCH_2P(S)Cl_2$ is isolated.

The above series of three experiments shows that $(CH_3)_2CHCH_2P(S)Cl_2$ is formed from $t\text{-}C_4H_9P(S)Cl_2$ under higher reaction temperature conditions.

EXAMPLE VI

A mixture of n-butyl chloride (92.6 g, 1 mole), $PCl_3$ (45.5 g, 0.333 mole), $P_4S_7$ (43.5 g, 0.125 mole) and $P_4S_3$ (9.2 g, 0.0418 mole) is heated in an autoclave at 295° C. for 12.5 hours. Upon cooling and venting, 4 g of lower boiling material and 0.27 mole (9.6 g) of HCl are collected. The product is poured out from the autoclave and weighs 167 g. This along with the HCl and the lower boiling material accounts for 180.6 g of the 191.1 g of original reactants used. The product is fractionally distilled collecting fractions: (1) b.p. 90-95 at 12 mm (71.7 g, $n_D^{25}$ 1.5278), (2) b.p. 65°-90° C. at 0.1 mm (12.6 g, $n_D^{25}$ 1.5328) and (3) b.p. 90°-180° C. at 0.1 mm (41.8 g). The residue weighs 23.6 g. There is also collected 10.5 g of volatile in the dry ice acetone cooled trap. The first fraction is analyzed by $^{31}P$ nmr and is shown to contain 44.0 g n-$C_4H_9P(S)Cl_2$ ($\delta P = 90.4$ ppm) and 27.7 g sec-$C_4H_9P(S)Cl_2$ ($\delta P = 104.7$ ppm). The 71.7 g of $C_4H_9P(S)Cl_2$ obtained represents a yield of 37.5% with a mole ratio of n-$C_4H_9P(S)Cl_2$ to sec-$C_4H_9P(S)Cl_2$ = 1:0.63. The 3rd fraction which weighs 41.8 g is further fractionated at 0.25 mm and the following fractions collected: (a) b.p. 60°-80° C., 2.0 g $n_D^{25}$ 1.5401, (b) b.p. 79°-110° C., 2.8 g, $n_D^{25}$ 1.5475. (c) b.p. 122° C., 7.6 g, $n_D^{25}$ 1.5628, (d) b.p. 134°-144° C., 2.8 g $n_D^{25}$ 1.6013, (e) b.p. 145°-152° C., 13 g, $n_D^{25}$ 1.6223 and (f) b.p. 152°-180° C., 6.7 g. The mass spectrum of fraction c indicates that it consists approximately of 95% $(C_4H_9)_2P(S)Cl$ in its various isomeric forms.

EXAMPLE VII

A mixture of n-octyl chloride (74.4 g, 0.5 mole), $PCl_3$ (23 g, 0.166 mole), $P_4S_7$ (21.8 g, 0.0625 mole), and $P_4S_3$ (4.6 g, 0.0209 mole) is heated at 270° C. for 12 hours. Upon venting, 0.085 mole (3.1 g) of HCl is collected. The reaction product poured out from the autoclave is a yellow liquid containing some yellow crystals. It weighs 115 g. This, along with the collected HCl, accounts for 118.1 g of the 123.8 g of reactants used. It is fractionally distilled. The first fraction, boils at 60°-96° C. at 0.05 mm and weighs 13 g, and is mainly unreacted n-octyl chloride. The second fraction, boils at 96°-135° C. at 0.05 mm and weighs 40 g. A third fraction, boils at 135°-190° C. at 0.05 mm, and weighs 18 g. All three fractions contain crystals. The residue remaining weighs 32 g. There is collected also in the dry-ice acetone-cooled trap a liquid weighing 12 g which, upon analysis by glc is shown to contain 7.8 g (0.057 mole) of unreacted $PCl_3$, 3 g (0.018 mole) of $PSCl_3$, and a small quantity of octyl chloride. Analysis by $^1H$ nmr shows that the octyl chloride is the unreacted n-octyl chloride and that there is also present in the fraction a small amount of octane.

The second fraction is shown by glc to contain four components with very close boiling points. The liquid portion is poured off from the solid and redistilled, collecting a center fraction with b.p. 72°-77° C. at 0.05 mm.

| Analysis |
|---|
| Calc'd for $C_8H_{17}P(S)Cl_2$; P, 12.5; S, 12.95; Cl, 28.7. |
| Found: P, 12.5; S, 12.1, Cl, 27.3. |

The results of this experiment indicate that approximately 18% of the original octyl chloride remains unreacted. The product, octylphosphonothionic dichloride, is a mixture of various isomers. The isomer ratios are determined by $^{13}C$ [$^1H$] nmr at 22-63 MHz, 6.5/$\mu$ sec. pulse width run with 50% (v/v)0.25M $Cr(acac)_3$ in $CoCl_3$ to remove NOE using a Bruker HFX-90/Diglab FTS/NMR-3.

There are four doublets (C-P coupling). The relative ratio of isomers of octylphosphonothionic dichloride and their $J_{CP}$ and chemical shifts are as follows:

| [$^1H$] Relative Area | $J_{CP(+Hz)}$ | TMS(=0.1 ppm) |
|---|---|---|
| $\alpha$5.5 | 72 | −54.8 |
| $\beta$2.0 | 66 | −56.8 |
| $\gamma$1.0 | 62 | −61.4 |
| $\delta$1.0 | 63 | −62.9 |

EXAMPLE VIII

A mixture of $C_6H_5CH_2Cl$ (63.3 g, 0.5 mole), $PCl_3$ (23 g, 0.166 mole), $P_4S_7$ (21.8 g, 0.0625 mole), and $P_4S_3$ (4.6 g, 0.0209 mole) is heated at 270° C. for 12 hours. Upon venting, 0.17 mole or 6.2 g of HCl is collected. The liquid reaction product poured out from the autoclave weighs 97 g. This, along with the HCl collected, accounts for 103.2 g of the 112.7 g of original reactants used. The product is fractionated. The first fraction, b.p. 95° C. at 0.1 mm, weighs 5 g. The second fraction, boiling at 95°-130° C. at 0.1 mm, weighs 28 g. A third fraction, b.p. 130°-160° C. at 0.1 mm, weighs 4 g. There are 43 g of residue and 17.0 g of liquid collected in the dry-ice acetone cooled trap. The liquid collected in the trap is shown by glc to contain 5.8 g (0.042 mole) of unreacted $PCl_3$, 9.4 g of $C_6H_5CH_3$, and small quantities of $P(S)Cl_3$ and $C_6H_5CH_2Cl$. The second fraction is redistilled, collecting a center fraction b.p. 72°-73° C. at 0.05 mm, $n_D^{25}$ 1.6123.

| Analysis |
|---|
| Calc'd. for $C_6H_5CH_2P(S)Cl_2$; P, 13.75; S, 14.2; Cl, 31.5. |
| Found: P, 13.3; S, 14.0; Cl, 30.6, |

$^1H$ nmr shows that the product consists of approximately 61% the expected $C_6H_5CH_2P(S)Cl_2$ and 39% $CH_3C_6H_4P(S)Cl_2$. Based on the original weight (28 g) of the second fraction, the combined yield of both $C_6H_5CH_2P(S)Cl_2$ and $CH_3C_6H_4P(S)Cl_2$ is only about 25%.

The above experiment using identical quantities of reactants is repeated under milder temperature conditions, i.e., by heating for 0.5 hr. at 255° C., followed by 12 hrs. at 220° C. Upon cooling and venting, no HCl gas is collected. The crude dark liquid reaction mixture weighs 111 g as compared to the total weight of 112.7 g of original reactants used. The mixture is distilled and a main fraction is collected, boiling at 95°-110° C. at 0.1 mm., $n_D^{25} = 1.6130$. Analysis by $^1H$ nmr indicates that it is predominantly $C_6H_5CH_2P(S)Cl_2$, the mole ratio $C_6H_5CH_2P(S)Cl_2$:$CH_3C_6H_4P(S)Cl_2$ being 29:1. It weighs 68 g or a yield of 61%. The lower boiling fraction and the volatiles collected in the dry-ice acetone-cooled trap have a combined weight of 10 g. Analysis by glc indicates four components, two of which are identified as $PCl_3$ and $C_6H_5CH_3$. The residue from this distillation weighs 29 g.

EXAMPLE IX

A mixture of $ClC_6H_4CH_3$ (63.3 g, 0.5 mole), $PCl_3$ (23 g, 0.166 mole), $P_4S_7$ (21.8 g, 0.0625 mole), and $P_4S_3$ (4.6 g, 0.0209 mole) is heated at 270° C. for 12 hours. Upon venting, 0.047 mole or 1.7 g of HCl is collected. The reaction product, an orange liquid, poured out from the autoclave, weighs 108 g (the weight of the original reactants is 112.7 g). It is fractionated. The first fraction, b.p. 45°-60° C. at 0.1 mm, weighs 5 g; the residue weighs 42 g. There is also collected in the cold trap a volatile fraction weighing 15 g which upon analysis by glc shows it to have the following composition: toluene, 6.5 g; $PCl_3$, 5.3 g; chlorotoluene, 2.6 g; the remainder being $P(S)Cl_3$. The second fraction obtained is further fractionated, collecting a fraction with a b.p. of 72°–75° C. at 2 mm. It weighs 28 g. Analysis by $^1H$ nmr shows it to contain $CH_3C_6H_4P(S)Cl_2$ and $C_6H_5CH_2P(S)Cl_2$ in a ratio of 4:1.

A repetition of the above experiment at a lower temperature i.e. 250° C. for 0.5 hr. and 220° C. for 12 hours results in mostly uncoverted $P_4S_{10}$ and p-chlorotoluene.

EXAMPLE X

In this experiment a reaction as shown in the following equation is carried out:

$$3CH_3Cl+PCl_3+0.286\ P_4S_3+0.214P_4S_{10}\rightarrow 3CH_3P(S)Cl_2$$

A mixture of methyl chloride (53 g, 1.05 mole) $PCl_3$ (45.6 g, 0.333 mole), $P_4S_3$ (20.9 g, 0.0953 mole), and $P_4S_{10}$ (31.7 g, 0.0713 mole) is heated at 340° C. for 2.75 hours. Upon venting, only a trace of HCl is collected. The liquid poured out from the autoclave weighs 143 g compared to the original input of 151.2 g of reactants. The product is analyzed by glc using hexadecane as the internal standard. The following results are obtained: $PCl_3$ (4.4 g, 0.032 mole), $P(S)Cl_3$ (4.6 g, 0.027 mole), $CH_3P(S)Cl_2$ (93.5 g, 0.627 mole), and $(CH_3)_2P(S)Cl$ (16.4 g, 0.128 mole). The yield of $CH_3P(S)Cl_2$ is 63% based on phosphorus.

EXAMPLE XI

In this experiment, a reaction as shown in the following equation is carried out:

$$3CH_3Br+PBr_3+0.375\ P_4S_7+0.125\ P_4S_3\rightarrow 3CH_3P(S)Br_2$$

In a 300 ml. stainless steel autoclave is placed 28.5 g (0.3 mole) of $CH_3Br$, 27.6 g (0.1 mole) of $PBr_3$, 13.1 g (0.0375 mole) of $P_4S_7$ and 2.7 g (0.0125 mole) of $P_4S_3$. The mixture is heated at 250° C. for 8 hours. Upon cooling and venting, there is only a trace of lower boiling material collected in the dry-ice acetone-cooled trap. Th product poured from the autoclave weighs 68 g as compared to the total input of 71.3 of reactants.

The product is fractionated into four main fractions at 10 mm pressure. (1) b.p. 54°–57° C., 17 g; (2) b.p. 75°–81° C., 4.2 g; (3) b.p. 81°–83° C. 9.5 g; (4) b.p. 83°–87° C., 23 g. The pressure is then reduced to 0.1 mm and a fraction weighing 2.6 g was obtained. The residue left weighs 40 g. Analysis by $^1H$ nmr of the second, third and fourth fractions shows them to contain a total of 29.4 g (0.104 mole) of $CH_3P(S)Br_2$ (J, 13.8:δ,3.23 ppm) and 7.3 g (0.042 mole) of $(CH_3)_2P(S)Br$, (J, 13.1;δ,2.51 ppm). The literature value reported for $(CH_3)_2P(S)Br$:J, 13.2; δ,2.15 ppm. The yield of $CH_3P(S)Br_2$ and $(CH_3)_2P(S)Br$ based on the phosphorus input are 35% and 14% respectively.

Having set forth the general nature and some examples of the present invention, the scope is now particularly set forth in the appended claims.

What is claimed is:

1. A method of preparing compounds of the formula:

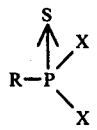

(I)

wherein R is a hydrocarbyl group consisting essentially of hydrogen and carbon including $C_1$ to $C_{20}$ alkyl; the aryl substituted derivatives thereof, said aryl having 1 or 2 fused rings, cycloalkyl of 5–6 carbons in the ring, aryl of up to 3 fused rings, biphenyl and the $C_1$–$C_4$ alkyl substituted derivatives of said cycloalkyl, aryl or biphenyl and X is chlorine or bromine, comprising contacting under at least an autogenous pressure *in a reaction zone capable of withstanding elevated pressure* at a temperature of from about 175° C. to about 400° C. in the presence of *combinations of* phosphorus sulfides an alkyl or aryl halide of the formula:

$$RX \qquad \text{(II)}$$

wherein R and X are as defined above with a trivalent phosphorus trihalide of the formula:

$$PX_3 \qquad \text{(III)}$$

or a pentavalent thiophosphoryl halide of the formula:

$$P(S)X_3 \qquad \text{(IV)}$$

or mixtures thereof wherein X is as defined above[.] *said reactants being contacted approximately according to the following general scheme:*

$$3RX + aPX_3 + bp(S)X_3 + \frac{[P_4S_{(6-2b)}]}{2} \rightarrow 3RP(S)X_2$$

*wherein R and X are as defined above and a plus b equals 1.*

2. The method of claim 1 wherein R is alkyl including methyl, ethyl, n-propyl and isopropyl, n-butyl, isobutyl, tert-butyl, pentyl, hexyl, heptyl, octyl, nonyl, decyl, dodecyl, tetradecyl, hexadecyl, octadecyl and eicosyl.

3. The method of claim 1 wherein R is aralkyl including phenylmethyl, phenylethyl, phenylbutyl, phenyloctyl, phenylhexadecyl, and the corresponding naphthyl derivatives.

4. The method of claim 1 wherein R is cycloalkyl including cyclopentyl and cyclohexyl and derivatives thereof.

5. The method of claim 1 wherein R is aryl including phenyl, methylphenyl, ethylphenyl, propylphenyl, and butylphenyl, naphthyl, methylnaphthyl, ethylnaphthyl, propylnaphthyl, butylnaphthyl, anthryl, methylanthryl, propylanthryl, butylanthryl, as well as dimethylphenyl, dimethylnaphthyl, diethylanthryl, biphenyl and derivatives thereof.

6. The method of claim 1 wherein said phosphorus sulfides include $P_4S_3$, $P_4S_5$, $P_4S_7$, or $P_4S_{10}$ and combinations thereof.

[7. The method of claim 1 wherein the reactants are contacted approximately according to the following general scheme:

$$3RX + aPX_3 + bP(S)X_3 + \frac{[P_4S_{(5-2b)}]}{2} \rightarrow 3RP(S)Cl_2 \qquad (5)$$

where R and X are as defined in claim 1 and a+b=1.]

* * * * *

UNITED STATES PATENT AND TRADEMARK OFFICE

CERTIFICATE OF CORRECTION

PATENT NO. : Re. 31,300

DATED : July 5, 1983

INVENTOR(S) : E. H. Uhing - A. D. F. Toy

It is certified that error appears in the above-identified patent and that said Letters Patent are hereby corrected as shown below:

Col. 3, line 67 - change "$P_4S_3$" to "$P_4S_7$"

Col. 5, line 8 - change "$C_2H_9P(S)Cl_2$" to "$C_4H_9P(S)Cl_2$"

Col. 8, line 8 - change "$C_2H_3P(S)Cl_2$" to "$C_2H_5P(S)Cl_2$"

Col. 8, line 9 - change "$(C_2H_3)_2P(S)Cl$" to "$(C_2H_5)_2P(S)Cl$"

Col. 9, line 51 - change "$J_{CH_3}$" to "$J_{\underline{C}H_3}$"

Col. 9, line 57 - change "$(CH_2)_3CP(S)Cl_2;P$," to "$(CH_3)_3CP(S)Cl_2:P$"

Col. 9, line 66 - change "$C_4H_9P(S)Cl_2;P$" to "$C_4H_9P(S)Cl_2:P$"

Col.10, line 6 - change "$J_{CH_3}$" to "$J_{\underline{C}H_3}$"

Col.11, line 50 - change "$C_8H_{17}P(S)Cl_2;P$" to "$C_8H_{17}P(S)Cl_2:P$"

Col.11, line 67 - change "TMS(=0.1ppm)" to "TMS($\pm$0.1ppm)"

Signed and Sealed this

*Twenty-eighth* Day of *August 1984*

[SEAL]

*Attest:*

GERALD J. MOSSINGHOFF

*Attesting Officer*

*Commissioner of Patents and Trademarks*